(12) United States Patent
Zafiroglu et al.

(10) Patent No.: US 10,238,337 B2
(45) Date of Patent: Mar. 26, 2019

(54) IN MOUTH WEARABLES FOR ENVIRONMENTAL SAFETY

(71) Applicant: Intel Corporation, Santa Clara, CA (US)

(72) Inventors: Alexandra C. Zafiroglu, Portland, OR (US); Giuseppe Raffa, Portland, OR (US); Stanley Mo, Hillsboro, OR (US); Joshua J. Ratcliff, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 777 days.

(21) Appl. No.: 14/229,591

(22) Filed: Mar. 28, 2014

(65) Prior Publication Data

US 2015/0272473 A1    Oct. 1, 2015

(51) Int. Cl.
*A61B 5/07* (2006.01)
*A61B 5/00* (2006.01)
*G06F 19/00* (2018.01)

(52) U.S. Cl.
CPC ............ *A61B 5/682* (2013.01); *A61B 5/4845* (2013.01); *G06F 19/3475* (2013.01); *A61B 5/6898* (2013.01); *A61B 2560/0242* (2013.01); *Y02A 90/26* (2018.01)

(58) Field of Classification Search
CPC combination set(s) only.
See application file for complete search history.

(56) References Cited

U.S. PATENT DOCUMENTS

| | | | | |
|---|---|---|---|---|
| 6,175,752 | B1* | 1/2001 | Say | A61M 5/1723 128/903 |
| 9,117,363 | B2* | 8/2015 | Kimmel | G08C 17/02 |
| 9,314,631 | B2* | 4/2016 | Avitall | A61N 1/36139 |
| 2007/0106138 | A1* | 5/2007 | Beiski | A61B 5/682 600/349 |
| 2012/0143021 | A1* | 6/2012 | Nagar | A61B 5/14532 600/301 |
| 2014/0248574 | A1* | 9/2014 | Yoon | A61C 13/01 433/8 |
| 2015/0305671 | A1* | 10/2015 | Yoon | A61B 5/01 600/301 |

FOREIGN PATENT DOCUMENTS

CN    102043893 A  *  5/2011  ............ Y02A 90/26

OTHER PUBLICATIONS

Roger Allen, "MEMS Helps Slash Food-Processing Analysis Costs," Electronic Design, Dec. 1, 2005, 6 pages.
(Continued)

*Primary Examiner* — Eric J Messersmith
(74) *Attorney, Agent, or Firm* — Jordan IP Law, LLC

(57) ABSTRACT

Systems and methods may provide for identifying sensor data associated with an intraoral device and analyzing a chemical composition of an ingestible product based on the sensor data. Additionally, a notification may be selectively generated based on the chemical composition. In one example, analyzing the chemical composition includes determining the level of one or more of an allergen, a toxin or a predetermined substance in the ingestible product.

22 Claims, 5 Drawing Sheets

(56) References Cited

OTHER PUBLICATIONS

Chris Buckley, "Rat Meat Sold as Lamb Highlights Fear in China," The New York Times, <http://www.nytimes.com/2013/05/04/world/asia/rat-meat-sold-as-lamb-in-china-highlights . . . >, May 3, 2013, 3 pages, New York.
Canada, "Canadian Standards (Maximum Levels) for Various Chemical Contaminants in Foods," <http://www.hc-sc.gc.ca/fn-an/securit/chem-chim/contaminants-guidelines-directives-eng.php>, Jun. 28, 2012, 4 pages, Canada.
Lakeshore, "China's Toxic Harvest: Growing Tainted Food in 'Cancer Villages'," Lakeshore Public Media, <http://lakeshorepublicmedia.org/stories/china-s-toxic-harvest-growing-tainted-food-in-cancer-villages . . . >, Apr. 16, 2013, 1 page.
Cheng-Yuan Li et al., "Sensor-Embedded Teeth for Oral Activity Recognition," 2013 International Symposium on Wearable Computers (Proceedings), 4 pages, New York.
Dean Nelson "Indian Head Teacher 'Deliberately' Poisoned School Meals, Killing 23 Children," Telegraph Media Group, Oct. 21, 2013, 2 pages, New Delhi.

\* cited by examiner

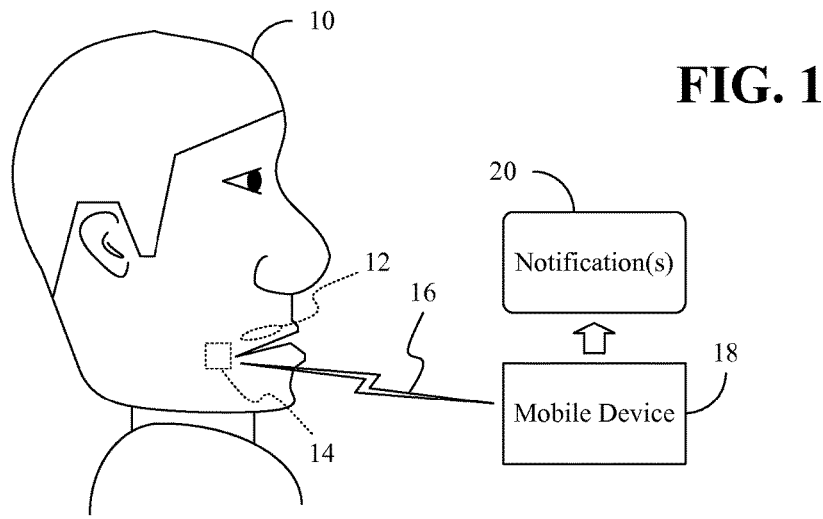
FIG. 1
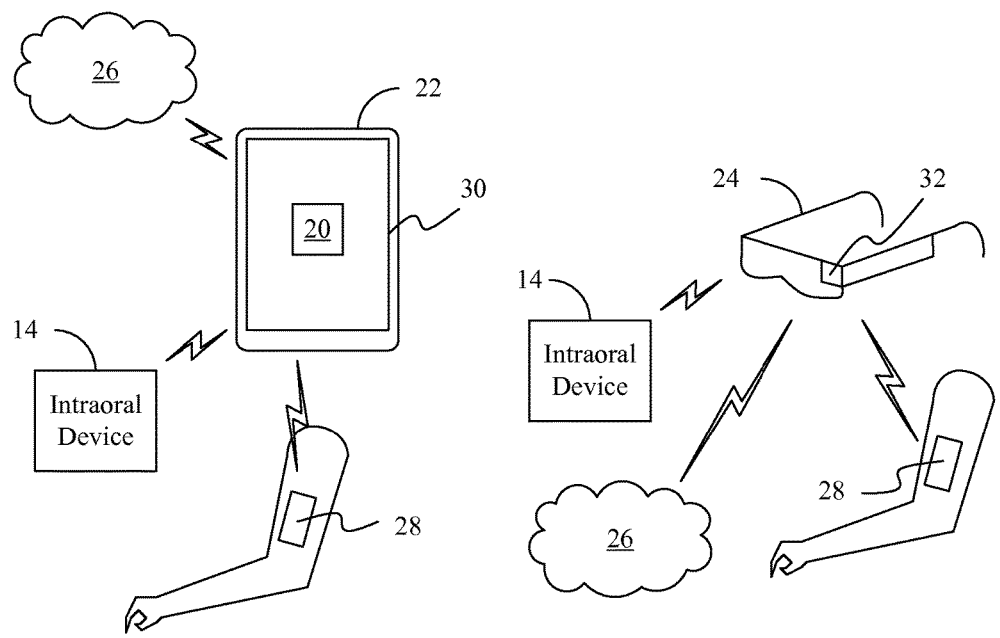
FIG. 2A
FIG. 2B

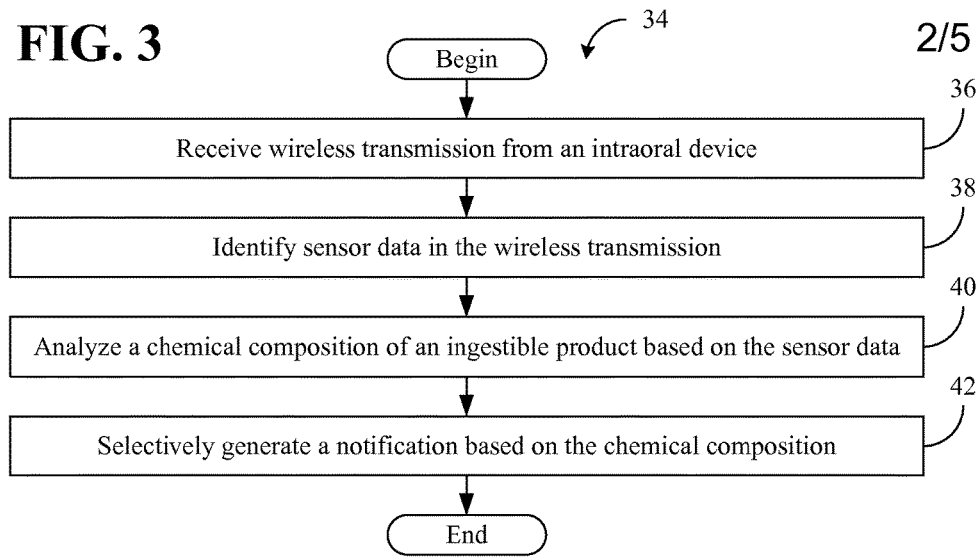
FIG. 3
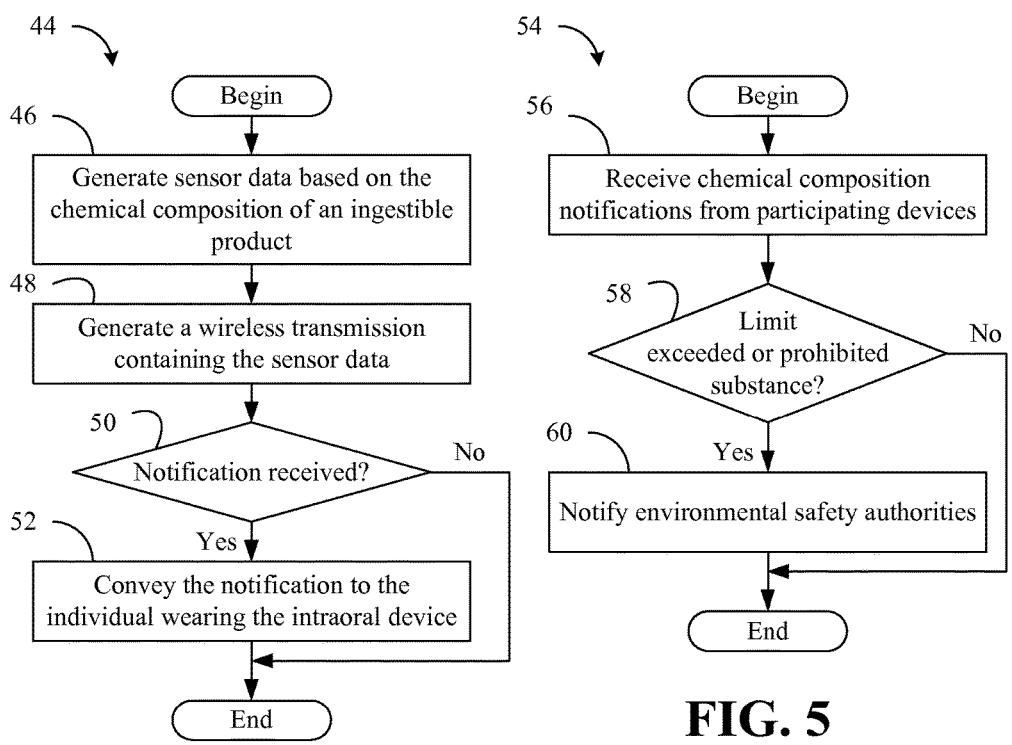
FIG. 4
FIG. 5

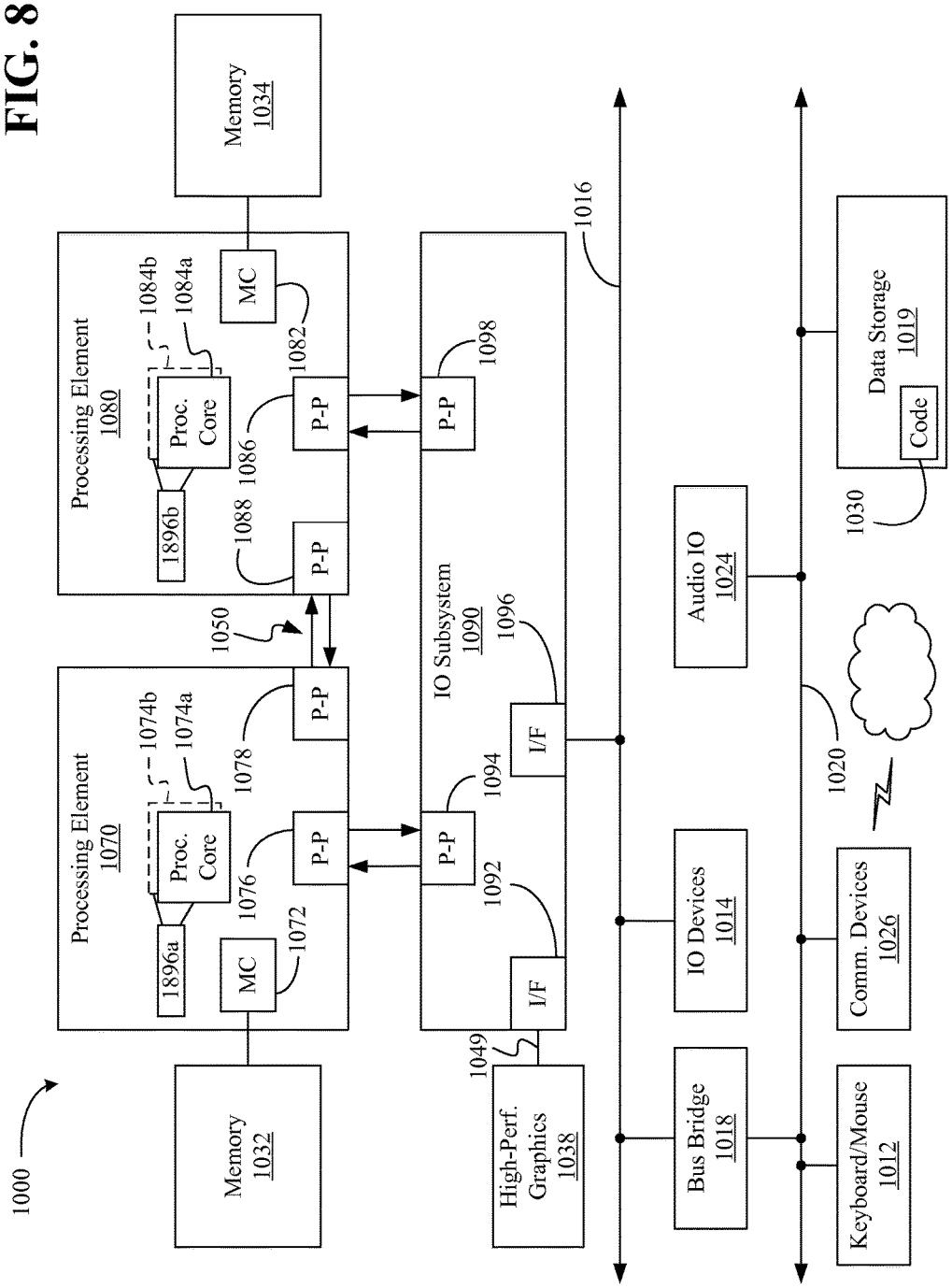

IN MOUTH WEARABLES FOR ENVIRONMENTAL SAFETY

TECHNICAL FIELD

Embodiments generally relate to the monitoring of ingestible products. More particularly, embodiments relate to the use of intraoral devices to monitor individual consumption of ingestible products.

BACKGROUND

Growing human populations have driven efforts to boost food production yields as well as an increased use of chemicals in the production of food. Unfortunately, a lack of transparency in global food production and distribution coupled with the increased use of chemicals may also cause considerable public health concerns. For example, in many instances, the only protective options available to consumers are relying on food labeling by producers and/or food testing by regulatory agencies, or buying directly from trusted local farmers. Those options may not always be effective, particularly when negligent and/or fraudulent food production practices exist.

BRIEF DESCRIPTION OF THE DRAWINGS

The various advantages of the embodiments will become apparent to one skilled in the art by reading the following specification and appended claims, and by referencing the following drawings, in which:

FIG. 1 is an illustration of an example of a wireless transmission between an intraoral device and a mobile device according to an embodiment;

FIGS. 2A and 2B are illustrations of examples of chemical composition notification approaches according to embodiments;

FIG. 3 is a flowchart of an example of a method of operating a mobile device according to an embodiment;

FIG. 4 is a flowchart of an example of a method of operating an intraoral device according to an embodiment;

FIG. 5 is a flowchart of an example of a method of operating a cloud computing infrastructure according to an embodiment;

FIG. 8 is a block diagram of an example of a system according to an embodiment.

DESCRIPTION OF EMBODIMENTS

Figure 6A:
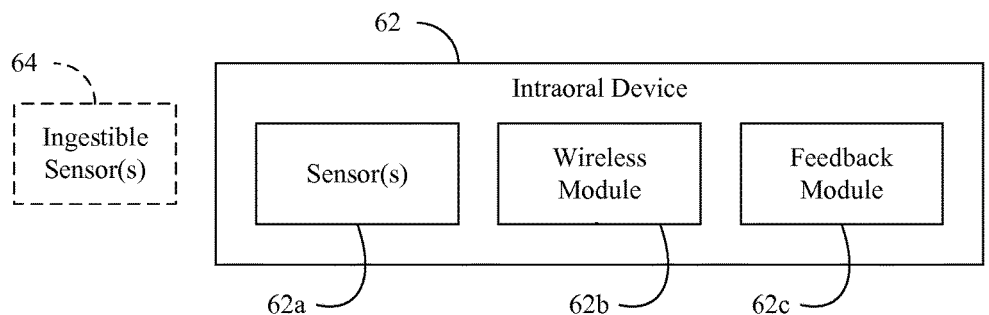
FIGS. 6A-6C are block diagrams of examples of logic architectures according to embodiments.

Turning now to FIG. 1, a scenario involving an individual 10 is shown in which the individual 10 either consumes or begins to consume an ingestible product 12 such as, for example, a food and/or beverage 12. The ingestible product 12 may also include other elements such as, for example, the air breathed by the individual, noxious chemicals in a cigarette smoked by the individual 10, and so forth. In the illustrated example, the individual 10 wears an intraoral device 14 (e.g., in mouth and/or nasal cavity "wearable"), which may include a removable device (e.g., dental retainer, tongue piercing, semi-permanent dental brace cemented to a tooth), an implant device (e.g., embedded in a tooth, soft palate, hard palate, gums, cheek interior), etc., or any combination thereof. As will be discussed in greater detail, the intraoral device 14 may generate sensor data (quantifying, e.g., osmotic permeability, ion levels, catalytic states, pH, optical polarizations) based on the chemical properties of the ingestible product 12 and incorporate the sensor data into one or more wireless transmissions 16 to a mobile device 18.

The mobile device 18, which may be carried by the individual 10, may receive the wireless transmissions 16, identify the sensor data in the wireless transmissions 16, analyze the chemical composition of the ingestible product 12 based on the sensor data, and selectively generate one or more notifications 20 based on the chemical composition. The chemical composition may identify, for example, toxin levels (e.g., mercury, lead, *Escherichia coli/E. coli, salmonella*, ricin, neurotoxin and/or necrotoxin content), allergen levels (e.g., peanut, shellfish, fish, wheat, soy, sulfites, eggs and/or dairy content), predetermined substance levels (e.g., alcohol, glucose/sugar and/or caffeine content), etc., or any combination thereof.

Additionally, the notifications 20 may be communicated to the individual 10 and/or other appropriate entity to ensure the safety of larger groups of people (e.g., communities, towns, cities, states). The mobile device 18 may also be used by the individual 10 to control the parameters (e.g., predefined substances, thresholds, limits, etc.) used to track and report chemical compositions. The wireless transmissions 16 (and/or wired transmissions) may be conducted in real-time or offline (e.g., stored locally and downloaded later), transferred to other wearable computing devices and/or individuals (e.g., where actions such as insulin adjustments may be taken), and so forth. Indeed, the functionality of the mobile device 18 may be incorporated into the intraoral device 14 (e.g., a combined intraoral/mobile device) depending upon the computing capacity of the intraoral device 14.

Accordingly, the illustrated approach ensures the safety of the ingestible product 12 to the individual 10 as well as to others even though producer labeling and/or regulatory agency testing of the ingestible product 12 may be nonexistent or unreliable (e.g., due to negligent and/or fraudulent food production practices). Indeed, the illustrated approach may enable the individual 10 to track dietary patterns not specifically related to safety (e.g., caffeine intake).

FIGS. 2A and 2B demonstrate that the mobile device 18 (FIG. 1) may take the form of a handheld device 22 (e.g., smart phone, tablet computer, notebook computer, personal digital assistant/PDA, mobile Internet device/MID) or a wearable device 24 (e.g., eyewear, head mounted display/HMD, watch, jewelry, clothing, accessories, footwear), respectively. More particularly, the illustrated handheld device 22 outputs one or more of the notifications 20 via a user interface (UI) such as, for example, a display 30, haptic (e.g., vibration) module, speaker, etc., or any combination thereof. Similarly, the wearable device 24 may be configured to output one or more of the notifications 20 via a UI 32 of the wearable device 24.

Additionally, the illustrated handheld device 22 and wearable device 24 are configured to send one or more of the notifications 20 back to the intraoral device 14, as well as to a remote server in a cloud computing infrastructure 26 and a bio tattoo 28 applied to a body part (e.g., arm, hand, wrist) of the individual 10 (FIG. 1). In this regard, the intraoral device 14, the bio tattoo 28 and the handheld device 22/wearable device 24 may form a wireless body area network (WBAN) that enables the individual to obtain real-time feedback about ingested and ingestible products, as well as control the parameters used to provide the feedback.

For example, the intraoral device 14 may use an internal feedback module (not shown) to communicate the notifications 20 to the individual 10 (FIG. 1) in the form of a change in texture, change in temperature, vibration, generation of a particular flavor, etc., or any combination thereof. Similarly, the bio tattoo 28 may include circuitry that conveys/communicates the notifications 20 to the individual 10 (FIG. 1) in the form of a change in texture, temperature and/or pressure (e.g., tightness against the skin) that may be detected by the individual 10 (FIG. 1).

Turning now to FIG. 3, a method 34 of operating a mobile device such as, for example, the mobile device 18 (FIG. 1), is shown. The method 34 may be implemented as one or more modules in set of logic instructions stored in a machine- or computer-readable storage medium such as random access memory (RAM), read only memory (ROM), programmable ROM (PROM), firmware, flash memory, etc., in configurable logic such as, for example, programmable logic arrays (PLAs), field programmable gate arrays (FPGAs), complex programmable logic devices (CPLDs), in fixed-functionality hardware logic using circuit technology such as, for example, application specific integrated circuit (ASIC), complementary metal oxide semiconductor (CMOS) or transistor-transistor logic (TTL) technology, or any combination thereof. For example, computer program code to carry out operations shown in method 34 may be written in any combination of one or more programming languages, including an object oriented programming language such as Java, Smalltalk, C++ or the like and conventional procedural programming languages, such as the "C" programming language or similar programming languages.

Illustrated processing block 36 provides for receiving a wireless transmission from an intraoral device such as, for example, the intraoral device 14 (FIGS. 1, 2A, 2B). The wireless transmission may be received via a Bluetooth (e.g., Institute of Electrical and Electronics Engineers/IEEE 802.15.1-2005, Wireless Personal Area Networks), near field communication (NFC), Wi-Fi (Wireless Fidelity, e.g., IEEE 802.11-2007, Wireless Local Area Network/LAN Medium Access Control (MAC) and Physical Layer (PHY) Specifications), or other type of wireless link. Sensor data may be identified in the wireless transmission at block 38, wherein identification of the sensor data may involve parsing packets, interpreting messages, analyzing header information, and so forth. As already noted, the sensor data may quantify various characteristics such as, for example, osmotic permeability, ion levels, catalytic states, pH, optical polarizations, etc., depending upon the type of sensor technology deployed in the intraoral device.

The chemical composition of an ingestible product is analyzed at block 40 based on the identified sensor data. Analyzing the chemical composition may include determining the level of specific allergens, toxins or other predetermined substances in the ingestible product. For example, the sensor data might indicate ion levels that are known to be found in a toxin such as mercury. In such a case, block 40 may involve matching the sensor data to the known toxin as well as determining the amount (e.g., parts per million/ppm) of that toxin in the ingestible product. In another example, the sensor data may indicate an osmotic permeability that is known to correspond to shellfish or other an allergen of the individual 10 (FIG. 1), wherein block 40 may match the sensor data to the known allergen and determine the amount of that allergen in the ingestible product. Moreover, the sensor data might indicate a catalytic state that is associated with caffeine or other predetermined substance, wherein block 40 might match the sensor data to the predetermined substance and determine the amount of the predetermined substance in the ingestible product. Simply put, the illustrated approach is able to differentiate between and measure different types of toxins, allergens and other substances in ingestible products.

A notification may be selectively generated at block 42 based on the chemical composition. Block 42 may include, for example, identifying a threshold (e.g., 10 ppm) in a user profile associated with the individual 10 (FIG. 1) and generating the notification if the level of the chemical composition exceeds the threshold. Thus, the user or a remote entity may establish certain thresholds based on the type of substance (e.g., any presence of toxins or allergens, moderate levels of other predetermined substances), wherein the triggering of the notification may be timestamped and specific to both the type of substance and its corresponding threshold (e.g., "Caffeine detected at 7:30 AM on Friday"). Moreover, the method 34 may be repeated so that the chemical composition of ingested products is tracked over time based on a plurality of wireless transmissions from the intraoral device (e.g., "Sugar consumption is too high this week"). The tracking time period may be also be set by the individual wearing the intraoral device (e.g., preceding 5 hrs, preceding 24 hrs, etc.) or a remote entity.

As already noted, the notifications may be sent in wireless transmissions (e.g., Bluetooth, NFC, Wi-Fi) to the intraoral device, a bio tattoo, a remote server, etc., or any combination thereof. Moreover, the notifications may be output via a user interface of a mobile device being carried by the individual wearing the intraoral device. One or more aspects of the method 34 may alternatively be performed by one or more remote servers of a cloud computing infrastructure such as the infrastructure 26 (FIGS. 2A and 2B), or other suitable computing device, depending upon the circumstances.

FIG. 4 shows a method 44 of operating an intraoral device such as, for example, the intraoral device 14 (FIGS. 1, 2A, 2B). The method 44 may be implemented as one or more modules in set of logic instructions stored in a machine- or computer-readable storage medium such as RAM, ROM, PROM, firmware, flash memory, etc., in configurable logic such as, for example, PLAs, FPGAs, CPLDs, in fixed-functionality hardware logic using circuit technology such as, for example, ASIC, CMOS or TTL technology, or any combination thereof. Illustrated block 46 provides for generating sensor data based on the chemical composition and/or properties of an ingestible product. As already noted, the sensor data may quantify various parameters (e.g., osmotic permeability, ion levels, catalytic states, pH, optical polarizations) that enable particular substances to be identified.

A wireless transmission containing the sensor data may be generated at block 48, wherein generation of the wireless transmission may involve constructing one or more packets and/or messages, depending on the type of wireless protocol being used as well as directing (e.g., addressing) the wireless transmission to a mobile device such as, for example, the mobile device 18 (FIG. 1). Illustrated block 50 determines whether a chemical composition notification (e.g., alert) has been received from the mobile device. If so, block 52 may convey/communicate the notification to the individual wearing the intraoral device. As already noted, the intraoral device may use an internal feedback module to communicate the notifications to the individual 10 in the form of a change in texture, change in temperature, vibration, generation of a particular flavor, etc., or any combination thereof.

FIG. 5 shows a method 54 of operating a cloud computing infrastructure such as, for example, the infrastructure 26 (FIGS. 2A, 2B). The method 54 may be implemented as one or more modules in set of logic instructions stored in a machine- or computer-readable storage medium such as RAM, ROM, PROM, firmware, flash memory, etc., in configurable logic such as, for example, PLAs, FPGAs, CPLDs, in fixed-functionality hardware logic using circuit technology such as, for example, ASIC, CMOS or TTL technology, or any combination thereof. Illustrated processing block 56 provides for receiving chemical composition notifications from participating devices such as, for example, the mobile device 18 (FIG. 1), wherein the received notifications may reflect the consumption levels of various substances across a group of people (e.g., community, town, city, state).

A determination may be made at block 58 as to whether any of the chemical consumption levels exceed a predetermined limit or correspond to a prohibited substance (e.g., deadly toxin). Block 58 may therefore involve conducting a geo-statistical analysis as to whether the group of people, or a subset thereof, has been ingesting abnormally high levels of one or more dangerous substances. If so, illustrated block 60 provides for notifying the appropriate environmental safety authorities of a potential public safety crisis and/or outbreak.

Turning now to FIG. 6A, a logic architecture 62 (62a-62c) that may be implemented in an intraoral device such as, for example, the intraoral device 14 (FIG. 1), already discussed, is shown. The logic architecture 26 may generally perform one or more aspects of the method 44 (FIG. 4), also already discussed. More particularly, the illustrated logic architecture 62 includes one or more sensors 62a to generate sensor data based on the chemical composition and/or properties of ingestible products. The sensors may include osmotic channel sensors, ion detection sensors (e.g., charge based), optical polarization sensors, direct contact sensors (e.g., pH, catalytic state, inductive, capacitive, sensitive panels/patches), spectrographs, etc., or any combination thereof. A wireless module 62b (e.g., Bluetooth, NFC, Wi-Fi) may generate wireless transmissions based on the sensor data, wherein generation of the wireless transmissions may include constructing one or more packets and/or messages, as well as directing the wireless transmissions to a mobile or other type of device.

A feedback module 62c may determine whether a chemical composition notification (e.g., alert) has been received from the mobile device. If so, the feedback module 62c may convey/communicate the notification to the individual wearing the intraoral device. The feedback module 62c may include, for example, haptic functionality to change the external texture of the intraoral device, change the temperature of the intraoral device, vibrate the intraoral device, emit a particular flavor from the intraoral device, etc., or any combination thereof.

The logic architecture 64 may also work in conjunction with an ingestible sensor 64 that may provide sensor data relating to internal organs (e.g., gastrointestinal/GI tract, esophagus, etc.). In such a case, the ingestible sensor 64 may wirelessly transmit the sensor data to the wireless module 62b, wherein the data received from the ingestible sensor may be combined with data obtained from the sensors 62a.

Figure 6B:
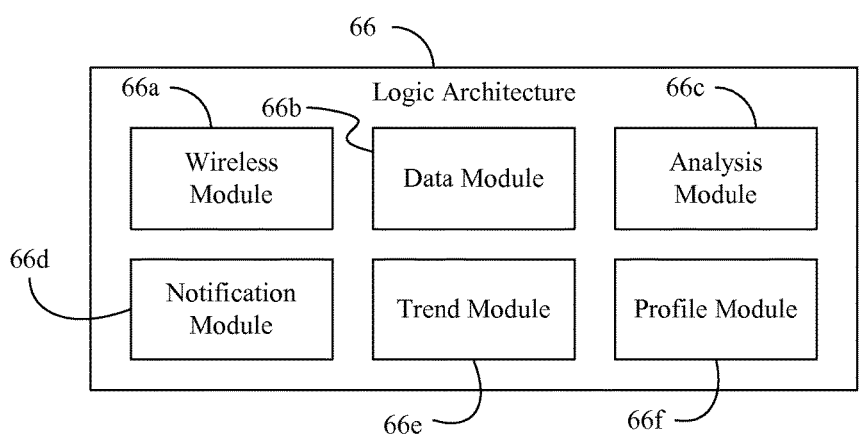

FIG. 6B shows a logic architecture 66 (66a-66f) that may be implemented in a mobile device such as, for example, the mobile device 18 (FIG. 1), already discussed. The logic architecture 66 may generally perform one or more aspects of the method 34 (FIG. 3), also already discussed. More particularly, the illustrated logic architecture 66 includes a wireless module 66a that receives wireless transmissions from an intraoral device worn by an individual. A data module 66b may identify sensor data in the wireless transmissions, wherein an analysis module 66c may analyze a chemical composition of an ingestible product based on the sensor data. The analysis module 66c may determine, for example, levels of specific allergens, toxins, predetermined substances, and so forth, in the ingestible product.

In one example, the architecture 66 includes a trend module 66e to track the chemical compositions of ingested products over time based on a plurality of wireless transmissions from the intraoral device. In this regard, the architecture 66 may store the sensor data and/or chemical composition information to an internal memory (not shown) for later retrieval, time-based analysis, report generation, and so forth.

The architecture 66 may also include a notification module 66d that selectively generates notifications based on the chemical compositions. The notification module 66d may output the notifications to a UI (not shown) of the mobile device. The notification module 66d may also use the wireless module 66b to send the notifications in wireless transmissions to the intraoral device, a bio tattoo, a remote server, etc., or any combination thereof. Additionally, a profile module 66f may identify one or more thresholds in a user profile associated with the individual wearing the intraoral device, wherein the notification module 66d generates the notifications if the levels of the chemical compositions exceed their respective thresholds. The profile module 66f may also establish, maintain and/or modify the user profile based on input from the individual operating the mobile device (or other connected device). Thus, the profile may identify specific toxins, allergens and/or predetermined substances, in addition to their respective thresholds, wherein the content of the user profile may be configurable by the individual in question.

Figure 6C:
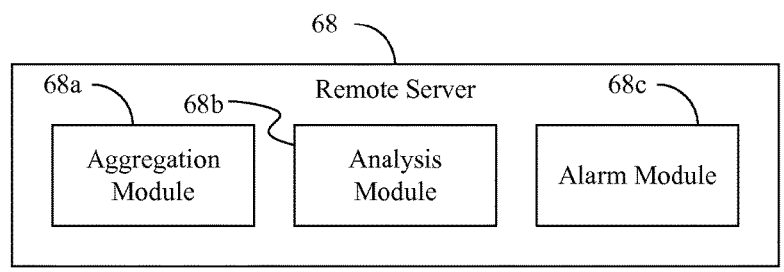

Turning now to FIG. 6C, a logic architecture 68 (68a-68c) that may be implemented in a remote server of a cloud computing infrastructure such as, for example, the infrastructure 26 (FIGS. 2A and 2B), already discussed, is shown. The logic architecture 68 may generally perform one or more aspects of the method 34 (FIG. 3) and/or the method 54 (FIG. 5). More particularly, the illustrated logic architecture 68 includes an aggregation module 68a to receive chemical composition notifications from a plurality of participating devices such as, for example, the mobile device 18 (FIG. 1), wherein the received notifications may indicate/reflect the consumption levels of various substances across a group of people (e.g., community, town, city, state).

An analysis module 68b may determine whether any of the chemical consumption levels exceed a predetermined limit or correspond to a prohibited substance (e.g., a safety condition exists with regard to the consumption levels). The architecture 68 may also include an alarm module 68c to notify the appropriate environmental safety authorities of a potential public safety crisis if a predetermined limit is exceeded or a prohibited substance is encountered.

Figure 7:
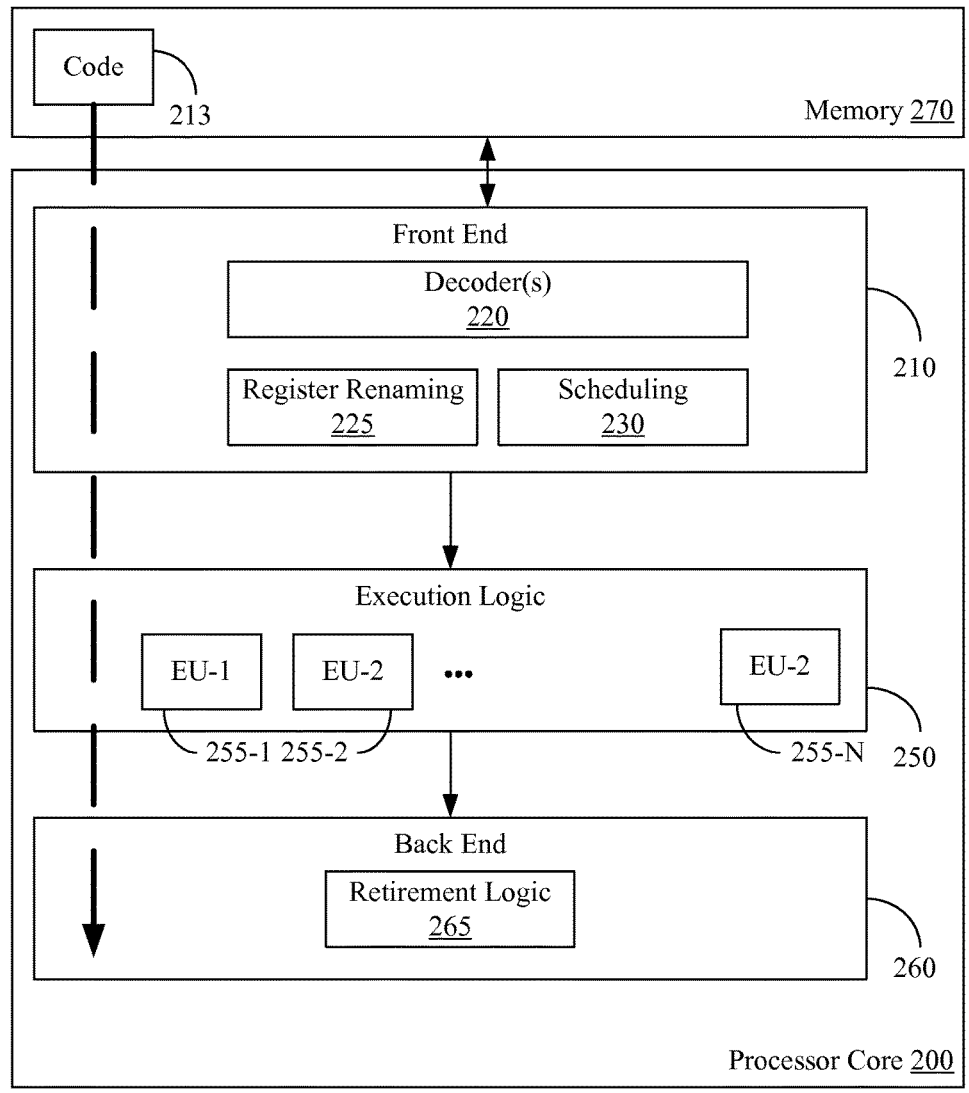
FIG. 7 is a block diagram of an example of a processor according to an embodiment.

FIG. 7 illustrates a processor core 200 according to one embodiment. The processor core 200 may be the core for any type of processor, such as a micro-processor, an embedded processor, a digital signal processor (DSP), a network processor, or other device to execute code. Although only one processor core 200 is illustrated in FIG. 7, a processing element may alternatively include more than one of the processor core 200 illustrated in FIG. 7. The processor core 200 may be a single-threaded core or, for at least one embodiment, the processor core 200 may be multithreaded in that it may include more than one hardware thread context (or "logical processor") per core.

FIG. 7 also illustrates a memory 270 coupled to the processor core 200. The memory 270 may be any of a wide variety of memories (including various layers of memory hierarchy) as are known or otherwise available to those of skill in the art. The memory 270 may include one or more code 213 instruction(s) to be executed by the processor core 200, wherein the code 213 may implement the method 34 (FIG. 3), the method 44 (FIG. 4), and/or the method 54 (FIG. 5), already discussed. The processor core 200 follows a program sequence of instructions indicated by the code 213. Each instruction may enter a front end portion 210 and be processed by one or more decoders 220. The decoder 220 may generate as its output a micro operation such as a fixed width micro operation in a predefined format, or may generate other instructions, microinstructions, or control signals which reflect the original code instruction. The illustrated front end 210 also includes register renaming logic 225 and scheduling logic 230, which generally allocate resources and queue the operation corresponding to the convert instruction for execution.

The processor core 200 is shown including execution logic 250 having a set of execution units 255-1 through 255-N. Some embodiments may include a number of execution units dedicated to specific functions or sets of functions. Other embodiments may include only one execution unit or one execution unit that can perform a particular function. The illustrated execution logic 250 performs the operations specified by code instructions.

After completion of execution of the operations specified by the code instructions, back end logic 260 retires the instructions of the code 213. In one embodiment, the processor core 200 allows out of order execution but requires in order retirement of instructions. Retirement logic 265 may take a variety of forms as known to those of skill in the art (e.g., re-order buffers or the like). In this manner, the processor core 200 is transformed during execution of the code 213, at least in terms of the output generated by the decoder, the hardware registers and tables utilized by the register renaming logic 225, and any registers (not shown) modified by the execution logic 250.

Although not illustrated in FIG. 7, a processing element may include other elements on chip with the processor core 200. For example, a processing element may include memory control logic along with the processor core 200. The processing element may include I/O control logic and/or may include I/O control logic integrated with memory control logic. The processing element may also include one or more caches.

Referring now to FIG. 8, shown is a block diagram of a system 1000 embodiment in accordance with an embodiment. Shown in FIG. 8 is a multiprocessor system 1000 that includes a first processing element 1070 and a second processing element 1080. While two processing elements 1070 and 1080 are shown, it is to be understood that an embodiment of the system 1000 may also include only one such processing element.

The system 1000 is illustrated as a point-to-point interconnect system, wherein the first processing element 1070 and the second processing element 1080 are coupled via a point-to-point interconnect 1050. It should be understood that any or all of the interconnects illustrated in FIG. 8 may be implemented as a multi-drop bus rather than point-to-point interconnect.

As shown in FIG. 8, each of processing elements 1070 and 1080 may be multicore processors, including first and second processor cores (i.e., processor cores 1074a and 1074b and processor cores 1084a and 1084b). Such cores 1074a, 1074b, 1084a, 1084b may be configured to execute instruction code in a manner similar to that discussed above in connection with FIG. 7.

Each processing element 1070, 1080 may include at least one shared cache 1896a, 1896b. The shared cache 1896a, 1896b may store data (e.g., instructions) that are utilized by one or more components of the processor, such as the cores 1074a, 1074b and 1084a, 1084b, respectively. For example, the shared cache 1896a, 1896b may locally cache data stored in a memory 1032, 1034 for faster access by components of the processor. In one or more embodiments, the shared cache 1896a, 1896b may include one or more mid-level caches, such as level 2 (L2), level 3 (L3), level 4 (L4), or other levels of cache, a last level cache (LLC), and/or combinations thereof.

While shown with only two processing elements 1070, 1080, it is to be understood that the scope of the embodiments are not so limited. In other embodiments, one or more additional processing elements may be present in a given processor. Alternatively, one or more of processing elements 1070, 1080 may be an element other than a processor, such as an accelerator or a field programmable gate array. For example, additional processing element(s) may include additional processors(s) that are the same as a first processor 1070, additional processor(s) that are heterogeneous or asymmetric to processor a first processor 1070, accelerators (such as, e.g., graphics accelerators or digital signal processing (DSP) units), field programmable gate arrays, or any other processing element. There can be a variety of differences between the processing elements 1070, 1080 in terms of a spectrum of metrics of merit including architectural, micro architectural, thermal, power consumption characteristics, and the like. These differences may effectively manifest themselves as asymmetry and heterogeneity amongst the processing elements 1070, 1080. For at least one embodiment, the various processing elements 1070, 1080 may reside in the same die package.

The first processing element 1070 may further include memory controller logic (MC) 1072 and point-to-point (P-P) interfaces 1076 and 1078. Similarly, the second processing element 1080 may include a MC 1082 and P-P interfaces 1086 and 1088. As shown in FIG. 8, MC's 1072 and 1082 couple the processors to respective memories, namely a memory 1032 and a memory 1034, which may be portions of main memory locally attached to the respective processors. While the MC 1072 and 1082 is illustrated as integrated into the processing elements 1070, 1080, for alternative embodiments the MC logic may be discrete logic outside the processing elements 1070, 1080 rather than integrated therein.

The first processing element 1070 and the second processing element 1080 may be coupled to an I/O subsystem 1090 via P-P interconnects 1076 1086, respectively. As shown in FIG. 8, the I/O subsystem 1090 includes P-P interfaces 1094 and 1098. Furthermore, I/O subsystem 1090 includes an interface 1092 to couple I/O subsystem 1090 with a high performance graphics engine 1038. In one embodiment, bus 1049 may be used to couple the graphics engine 1038 to the I/O subsystem 1090. Alternately, a point-to-point interconnect may couple these components.

In turn, I/O subsystem 1090 may be coupled to a first bus 1016 via an interface 1096. In one embodiment, the first bus 1016 may be a Peripheral Component Interconnect (PCI) bus, or a bus such as a PCI Express bus or another third generation I/O interconnect bus, although the scope of the embodiments are not so limited.

As shown in FIG. 8, various I/O devices 1014 (e.g., cameras, sensors) may be coupled to the first bus 1016, along with a bus bridge 1018 which may couple the first bus 1016 to a second bus 1020. In one embodiment, the second bus 1020 may be a low pin count (LPC) bus. Various devices may be coupled to the second bus 1020 including, for example, a keyboard/mouse 1012, network controllers/communication device(s) 1026 (which may in turn be in communication with a computer network), and a data storage unit 1019 such as a disk drive or other mass storage device which may include code 1030, in one embodiment. The code 1030 may include instructions for performing embodiments of one or more of the methods described above. Thus, the illustrated code 1030 may implement the method 34 (FIG. 3), the method 44 (FIG. 4), and/or the method 54 (FIG. 5), already discussed, and may be similar to the code 213 (FIG. 7), already discussed. Further, an audio I/O 1024 may be coupled to second bus 1020.

Note that other embodiments are contemplated. For example, instead of the point-to-point architecture of FIG. 8, a system may implement a multi-drop bus or another such communication topology. Also, the elements of FIG. 8 may alternatively be partitioned using more or fewer integrated chips than shown in FIG. 8.

Additional Notes and Examples

Example 1 may include a system to enhance environmental safety, comprising a mobile device including a first wireless module to receive a wireless transmission from an intraoral device, a data module to identify sensor data in the wireless transmission, a data module to identify the sensor data in the wireless transmission, an analysis module to analyze a chemical composition of an ingestible product based on the sensor data, and a notification module to selectively generate a notification based on the chemical composition.

Example 2 may include the system of Example 1, wherein the analysis module is to determine a level of one or more of an allergen, a toxin or a predetermined substance in the ingestible product.

Example 3 may include the system of Example 1, wherein the notification module is to use the second wireless module to send the notification in a wireless transmission to one or more of the intraoral device, a bio tattoo or a remote server.

Example 4 may include the system of Example 1, wherein the mobile device further includes a user interface, and wherein the notification module is to output the notification via the user interface.

Example 5 may include the system of Example 1, wherein the mobile device further includes a trend module to track a chemical composition of ingested products over time based on a plurality of wireless transmissions from the intraoral device.

Example 6 may include the system of any one of Examples 1 to 5, wherein the mobile device further includes a profile module to identify a threshold in a user profile associated with an individual wearing the intraoral device, wherein the notification module is to generate the notification if a level of the chemical composition exceeds the threshold.

Example 7 may include the system of any one of Examples 1 to 5, further including the intraoral device, wherein the intraoral device has a sensor to generate the sensor data and a second wireless module to generate the wireless transmission containing the sensor data, the intraoral device includes one of a removable device or an implant device, and the mobile device includes one or more of a wearable device or a handheld device.

Example 8 may include a method of operating a mobile device, comprising identifying sensor data associated with an intraoral device, analyzing a chemical composition of an ingestible product based on the sensor data, and selectively generating a notification based on the chemical composition.

Example 9 may include the method of Example 8, wherein analyzing the chemical composition includes determining a level of one or more of an allergen, a toxin or a predetermined substance in the ingestible product.

Example 10 may include the method of Example 8, further including sending the notification in a wireless transmission to one or more of the intraoral device, a bio tattoo or a remote server.

Example 11 may include the method of Example 8, further including outputting the notification via a user interface of the mobile device.

Example 12 may include the method of Example 8, further including tracking a chemical composition of ingested products over time based on a plurality of wireless transmissions from the intraoral device.

Example 13 may include the method of any one of Examples 8 to 12, wherein selectively generating the notification includes identifying a threshold in a user profile associated with an individual wearing the intraoral device; and generating the notification if a level of the chemical composition exceeds the threshold.

Example 14 may include at least one computer readable storage medium comprising a set of instructions which, when executed by a mobile device, cause the mobile device to identify sensor data associated with an intraoral device, analyze a chemical composition of an ingestible product based on the sensor data, and selectively generate a notification based on the chemical composition.

Example 15 may include the at least one computer readable storage medium of Example 14, wherein the instructions, when executed, cause the mobile device to determine a level of one or more of an allergen, a toxin or a predetermined substance in the ingestible product.

Example 16 may include the at least one computer readable storage medium of Example 14, wherein the instructions, when executed, cause the mobile device to send the notification in a wireless transmission to one or more of the intraoral device, a bio tattoo or a remote server.

Example 17 may include the at least one computer readable storage medium of Example 14, wherein the instructions, when executed, cause the mobile device to output the notification via a user interface of the mobile device.

Example 18 may include the at least one computer readable storage medium of Example 14, wherein the instructions, when executed, cause the mobile device to track a chemical composition of ingested products over time based on a plurality of wireless transmissions from the intraoral device.

Example 19 may include the at least one computer readable storage medium of any one of Examples 14 to 18, wherein the instructions, when executed, cause the mobile device to identify a threshold in a user profile associated with an individual wearing the intraoral device; and generate the notification if a level of the chemical composition exceeds the threshold.

Example 20 may include an intraoral device comprising one or more sensors to generate sensor data based on a chemical composition of an ingestible product; and a wireless module to generate a wireless transmission based on the sensor data.

Example 21 may include the intraoral device of Example 20, wherein the wireless module is to receive a chemical composition notification, the intraoral device further including a feedback module to convey the chemical composition notification to an individual wearing the intraoral device.

Example 22 may include a method of operating an intraoral device, comprising generating sensor data based on a chemical composition of an ingestible product; and generating a wireless transmission based on the sensor data.

Example 23 may include the method of Example 22, further including receiving a chemical composition notification; and conveying the chemical composition notification to an individual wearing the intraoral device.

Example 24 may include at least one computer readable storage medium comprising a set of instructions which, when executed by an intraoral device, cause the intraoral device to generate sensor data based on a chemical composition of an ingestible product; and generate a wireless transmission based on the sensor data.

Example 25 may include the at least one computer readable storage medium of Example 24, wherein the instructions, when executed by a processor, cause the intraoral device to receive a chemical composition notification; and convey the chemical composition notification to an individual wearing the intraoral device.

Example 26 may include a server of a cloud computing infrastructure, comprising an aggregation module to receive chemical composition notifications from a plurality of devices, wherein the chemical composition notifications indicate consumption levels of one or more specific substances across a group of people; an analysis module to determine whether a safety condition exists with regard to the consumption levels; and an alert module to notify an environmental safety authority if the safety condition exists.

Example 27 may include the server of Example 26, wherein the safety condition is to include one or more of the consumption levels exceeding a predetermined limit or the consumption levels corresponding to a prohibited substance.

Example 28 may include a method of operating a server of a cloud computing infrastructure, comprising receiving chemical composition notifications from a plurality of devices, wherein the chemical composition notifications indicate consumption levels of one or more substances across a group of people; determining whether a safety condition exists with regard to the consumption levels; and notifying an environmental safety authority if the safety condition exists.

Example 29 may include the method of Example 28, wherein the safety condition includes one or more of the consumption levels exceeding a predetermined limit or the consumption levels corresponding to a prohibited substance.

Example 30 may include at least one computer readable storage medium comprising a set of instructions which, when executed by a server, cause the server to receive chemical composition notifications from a plurality of devices, wherein the chemical composition notifications indicate consumption levels of one or more substances across a group of people; determine whether a safety condition exists with regard to the consumption levels; and notify an environmental safety authority if the safety condition exists.

Example 31 may include the at least one computer readable storage medium of Example 30, wherein the safety condition is to include one or more of the consumption levels exceeding a predetermined limit or the consumption levels corresponding to a prohibited substance. Example 39 may include an intraoral device comprising means for generating sensor data based on a chemical composition of an ingestible product; and means for generating a wireless transmission based on the sensor data.

Example 40 may include the intraoral device of Example 39, further including means for receiving a chemical composition notification; and means for conveying the chemical composition notification to an individual wearing the intraoral device. Example 41 may include a server comprising means for receiving chemical composition notifications from a plurality of devices, wherein the chemical composition notifications indicate consumption levels of one or more substances across a group of people; means for determining whether a safety condition exists with regard to the consumption levels; and means for notifying an environmental safety authority if the safety condition exists.

Example 42 may include the server of Example 41, wherein the safety condition is to include one or more of the consumption levels exceeding a predetermined limit or the consumption levels corresponding to a prohibited substance.

Thus, techniques described herein may leverage intraoral wearable computing devices to provide individuals with information and alerts about the chemical makeup of the foods and beverages they consume. The information and alerts may include, but are not limited to, the types and levels of toxins and allergens in ingested substances, wherein the feedback may be immediate. Accordingly, individuals may be able to make more informed decisions about the risks posed by foods and beverages. The techniques may be useful to diabetics and the general population from both a safety standpoint and a dietary standpoint (e.g., staying within recommended daily limits set by health institutions and/or physicians).

Embodiments are applicable for use with all types of semiconductor integrated circuit ("IC") chips. Examples of these IC chips include but are not limited to processors, controllers, chipset components, programmable logic arrays (PLAs), memory chips, network chips, systems on chip (SoCs), SSD/NAND controller ASICs, and the like. In addition, in some of the drawings, signal conductor lines are represented with lines. Some may be different, to indicate more constituent signal paths, have a number label, to indicate a number of constituent signal paths, and/or have arrows at one or more ends, to indicate primary information flow direction. This, however, should not be construed in a limiting manner. Rather, such added detail may be used in connection with one or more exemplary embodiments to facilitate easier understanding of a circuit. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/or single-ended lines.

Example sizes/models/values/ranges may have been given, although embodiments are not limited to the same. As manufacturing techniques (e.g., photolithography) mature over time, it is expected that devices of smaller size could be manufactured. In addition, well known power/ground connections to IC chips and other components may or may not be shown within the figures, for simplicity of illustration and discussion, and so as not to obscure certain aspects of the embodiments. Further, arrangements may be shown in block diagram form in order to avoid obscuring embodiments, and also in view of the fact that specifics with respect to implementation of such block diagram arrangements are highly dependent upon the platform within which the embodiment is to be implemented, i.e., such specifics should be well within purview of one skilled in the art. Where specific details (e.g., circuits) are set forth in order to describe example embodiments, it should be apparent to one skilled in the art that embodiments can be practiced without, or with variation of, these specific details. The description is thus to be regarded as illustrative instead of limiting.

The term "coupled" may be used herein to refer to any type of relationship, direct or indirect, between the components in question, and may apply to electrical, mechanical, fluid, optical, electromagnetic, electromechanical or other connections. In addition, the terms "first", "second", etc. may be used herein only to facilitate discussion, and carry no particular temporal or chronological significance unless otherwise indicated.

As used in this application and in the claims, a list of items joined by the term "one or more of" may mean any combination of the listed terms. For example, the phrases "one or more of A, B or C" may mean A; B; C; A and B; A and C; B and C; or A, B and C.

Those skilled in the art will appreciate from the foregoing description that the broad techniques of the embodiments can be implemented in a variety of forms. Therefore, while the embodiments have been described in connection with particular examples thereof, the true scope of the embodiments should not be so limited since other modifications will become apparent to the skilled practitioner upon a study of the drawings, specification, and following claims.

We claim:

1. A system comprising:
  a mobile device including,
    first wireless logic, implemented at least partly in one or more of configurable logic or fixed functionality logic circuitry, to receive a wireless transmission from an intraoral device,
    data logic, implemented at least partly in one or more of configurable logic or fixed functionality logic circuitry, to identify sensor data in the wireless transmission,
    analysis logic, implemented at least partly in one or more of configurable logic or fixed functionality logic circuitry, to,
      analyze a chemical composition of an ingestible product based on the sensor data,
      determine a composition level of one or more ingestible substances, and
      determine whether the composition level of the one or more ingestible substances exceeds a threshold across a group of people, and
    notification logic, implemented at least partly in one or more of configurable logic or fixed functionality logic circuitry, to communicate a notification to the intraoral device to notify a user of the intraoral device when the threshold is exceeded.

2. The system of claim 1, wherein the analysis logic is to determine a level of one or more of an allergen, a toxin or a predetermined substance in the ingestible product.

3. The system of claim 1, wherein the notification logic is to use a second wireless module to send the notification in a wireless transmission to one or more of the intraoral device, a bio tattoo or a remote server.

4. The system of claim 1, wherein the mobile device further includes a user interface, and wherein the notification logic is to output the notification via the user interface.

5. The system of claim 1, wherein the mobile device further includes trend logic, implemented at least partly in one or more of configurable logic or fixed functionality logic circuitry, to track a chemical composition of ingested products over time based on a plurality of wireless transmissions from the intraoral device.

6. The system of claim 1, further including the intraoral device, wherein the intraoral device has a sensor to generate the sensor data and second wireless logic, implemented at least partly in one or more of configurable logic or fixed functionality logic circuitry, to generate the wireless transmission containing the sensor data, the intraoral device includes one of a removable device or an implant device, and the mobile device includes one or more of a wearable device or a handheld device.

7. A method comprising:
  identifying sensor data associated with an intraoral device;
  analyzing external to the intraoral device a chemical composition of an ingestible product based on the sensor data;
  determining a composition level of one or more ingestible substances;
  determining whether the composition level of the one or more ingestible substances exceeds a threshold across a group of people; and
  communicating a notification to the intraoral device to notify a user of the intraoral device when the threshold is exceeded.

8. The method of claim 7, wherein analyzing the chemical composition includes determining a level of one or more of an allergen, a toxin or a predetermined substance in the ingestible product.

9. The method of claim 7, further including sending the notification in a wireless transmission to one or more of a bio tattoo or a remote server.

10. The method of claim 7, further including outputting the notification via a user interface of a mobile device.

11. The method of claim 7, further including tracking a chemical composition of ingested products over time based on a plurality of wireless transmissions from the intraoral device.

12. At least one computer readable storage medium comprising a set of instructions which, when executed by a mobile device, cause the mobile device to:
  identify sensor data associated with an intraoral device;
  analyze a chemical composition of an ingestible product based on the sensor data,
  determine a composition level of one or more ingestible substances;
  determine whether the composition level of the one or more ingestible substances exceeds a threshold across a group of people; and
  communicate a notification to the intraoral device to notify a user of the intraoral device when the threshold is exceeded.

13. The at least one computer readable storage medium of claim 12, wherein the instructions, when executed, cause the mobile device to determine a level of one or more of an allergen, a toxin or a predetermined substance in the ingestible product.

14. The at least one computer readable storage medium of claim 12, wherein the instructions, when executed, cause the mobile device to send the notification in a wireless transmission to one or more of a bio tattoo or a remote server.

15. The at least one computer readable storage medium of claim 12, wherein the instructions, when executed, cause the mobile device to output the notification via a user interface of the mobile device.

16. The at least one computer readable storage medium of claim 12, wherein the instructions, when executed, cause the mobile device to track a chemical composition of ingested products over time based on a plurality of wireless transmissions from the intraoral device.

17. An intraoral device comprising:
one or more sensors to generate sensor data based on a chemical composition of an ingestible product; and
wireless logic, implemented at least partly in one or more of configurable logic or fixed functionality logic circuitry, to:
generate a wireless transmission based on the sensor data; and
receive a notification to notify a user of the intraoral device when a threshold across a group of people is exceeded, wherein the notification is to be generated based on an identification of the sensor data in the wireless transmission, an analysis of the chemical composition based on the sensor data, a determination of a consumption level of one or more ingestible substances, and a determination whether the composition level of the one or more ingestible substances exceeds the threshold.

18. At least one computer readable storage medium comprising a set of instructions which, when executed by an intraoral device, cause the intraoral device to:
generate sensor data based on a chemical composition of an ingestible product;
generate a wireless transmission based on the sensor data; and
receive a notification to notify a user of the intraoral device when a threshold across a group of people is exceeded, wherein the notification is to be generated based on an identification of the sensor data in the wireless transmission, an analysis of the chemical composition based on the sensor data, a determination of a consumption level of one or more ingestible substances, and a determination whether the composition level of the one or more ingestible substances exceeds the threshold.

19. The system of claim 1, wherein the sensor data is to include a catalytic state associated with the one or more ingestible substances.

20. The system of claim 1, wherein the notification logic is further to send a notification to a remote server to implement a geo-statistical analysis to determine whether the consumption level is to exceed the threshold.

21. The system of claim 1, wherein the notification logic is further to send a notification to a remote server to alert a safety authority of a potential public safety crisis.

22. The system of claim 1, further including a feedback module to emit a particular flavor from the intraoral device in response to the notification.

* * * * *